United States Patent [19]

Ballnus

[11] 4,333,838
[45] Jun. 8, 1982

[54] METHOD AND APPARATUS FOR PURIFYING AN ACTIVATED SLUDGE-WASTE WATER MIXTURE

[75] Inventor: Wilhelm Ballnus, Burgwedel, Fed. Rep. of Germany

[73] Assignee: Schreiber-Kläranlagen Dr.-Ing. Aug. Schreiber GmbH & Co. KG, Langenhage, Fed. Rep. of Germany

[21] Appl. No.: 247,223

[22] Filed: Mar. 24, 1981

[30] Foreign Application Priority Data

Mar. 24, 1980 [DE] Fed. Rep. of Germany ....... 3011247

[51] Int. Cl.³ .............................................. C02F 3/26
[52] U.S. Cl. .................................... 210/614; 210/627; 210/745; 210/96.1
[58] Field of Search ............... 210/607, 614, 620–627, 210/745, 94, 96.1, 194, 195.3, 205, 143

[56] References Cited

U.S. PATENT DOCUMENTS

| 2,154,132 | 4/1939 | Mallory | 210/614 |
| 3,979,290 | 9/1976 | Löffler | 210/745 |
| 4,116,832 | 9/1978 | Tardivel | 210/745 |

FOREIGN PATENT DOCUMENTS 55-152510  11/1980  Japan .................................. 210/745

Primary Examiner—Thomas G. Wyse
Attorney, Agent, or Firm—Watson, Cole, Grindle & Watson

[57] ABSTRACT

A method and apparatus is disclosed for purifying the waste water in an activated sludge-waste water mixture. In dependence upon the state of purification of the waste water, the mixture is ventilated in automatically controlled manner by a gas comprising molecular oxygen. The automatic control of ventilation is exercised by the use of a monitoring device which measures the visible depth of the waste water and, depending upon the measured value, starts-up or switches-off the ventilation.

13 Claims, 2 Drawing Figures

METHOD AND APPARATUS FOR PURIFYING AN ACTIVATED SLUDGE-WASTE WATER MIXTURE

This invention relates to a method of purifying an activated sludge-waste water mixture, in which a gas comprising molecular oxygen is automatically introduced by controlling the ventilation intensity, and to an activated sludge-waste water purifying apparatus having a controllable ventilating device for the automatic introduction of molecular oxygen into at least one activating tank.

The purification of waste water by means of activated sludge has given technically satisfactory results. It is necessary in the process to control the oxygen content in a minimum of one activating tank. Control is normally effected by measuring the actual oxygen content and by ventilating the activating tank in dependence on the measured value. The purification corresponds to the state of load. In plants with a very low load, purification with values of up to approximately 5 mg BOD/1 is thereby possible. However, extensive purification of this type uses up a great deal of power and is for the most part unnecessary. Moreover, in the known method of procedure, a measurable oxygen content is absolutely necessary in the waste water or respectively in the activating tank, since otherwise measurement can no longer be carried out. With this, however, even the oxygen supply can no longer be directly reduced. Further, measuring the oxygen content is very complicated and expensive, and requires great expense for operational security. Control of the ventilating device for introducing the necessary oxygen is also of a corresponding expense.

It is therefore an object of the invention to provide a method and apparatus of the above-named type in such a way that relatively simple control is possible.

The invention uses as a starting point the knowledge that the visible depth or respectively the clarity of the waste water is in close relationship to the desired or necessary purification.

According to one aspect the invention provides a method of purifying an activated sludge-waste water mixture, which comprises the introduction of a gas comprising molecular oxygen to the mixture in an automatically controlled manner in dependence upon the state of purification of the waste water;
in which the state of purification of the waste water is monitored by measuring the visible depth of the waste water and, depending upon this measurement, appropriate control is applied automatically over the introduction of the gas to the mixture.

According to a further aspect the invention provides an activated sludge-waste water purifying apparatus comprising:
a tank for holding an activated sludge-waste water mixture;
a controllable ventilating device for introducing automatically a gas comprising molecular oxygen to said mixture in dependence upon the state of purification of the waste water;
a monitoring device for measuring the visible depth of the waste water;
and control means for controlling the operation of the ventilating device in dependence upon the measured value of the visible depth.

A fundamental aspect of the invention is that for optimal control of the activating tank, the visible depth or respectively clarify of the waste water is measured and not, as previously, the oxygen content itself. Measuring the visible depth can be carried out relatively simply, for example by means of photocells or similar photoelectric devices, whereby the thereby gained electrical output signals can be used directly for controlling, in particular for switching on or off, the ventilating device. In the case of a two-point control, the appropriate values, at which the ventilating device is switched on or off, are first determined experimentally for each plant to be put into operation, i.e., according to the desired degree of purification, an upper visible depth switching point is determined for switching off the ventilation, and a lower visible depth switching point is determined for switching on or connecting the ventilation.

Although the visible depth of the outflow of the resettling tank can be used, very large time differences would result for changes in load during the time of the through-flow through the treatment plant to the resettling tank, so that fluctuations in load can no longer be followed. It is therefore advantageous to remove an activated sludge-waste water mixture from the activating tank, to desludge this in a bypass arrangement by means of a sludge separating device, then to measure the visible depth, and then to feed it back to the ventilating tank or activating tank or to the treatment plant supply.

DESCRIPTION OF PREFERRED EMBODIMENT

Figure 1:
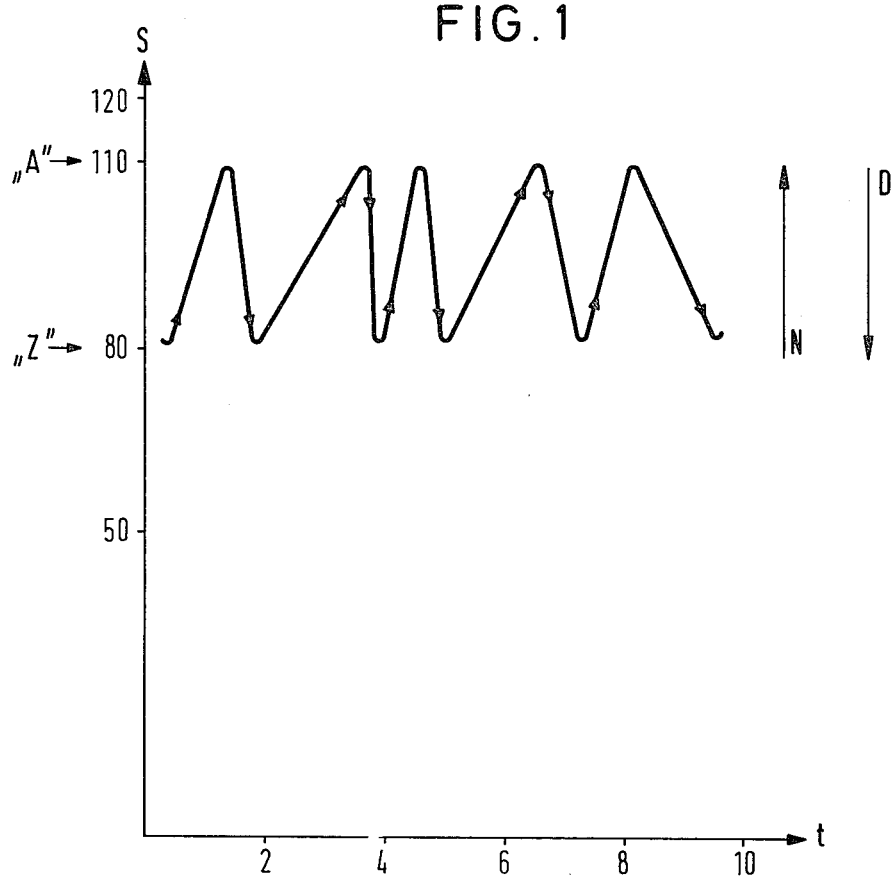
FIG. 1 is a graph of a model course of operation with the application of a method according to the invention with a two-point control.

In FIG. 1, the time t is entered in hours along the abscissa and the visible depth s is entered in centimeters along the ordinate. Photoelectric devices, preferably photocells, are particularly suitable for measuring the visible depth. Photocells emit an electrical output signal, which can be used further, in dependence on the incoming light intensity, and therefore on the visible depth. Although the electrical output signal of the photocells can be processed further analogically, it is however suitable to carry out a two-point control, whereby a ventilating device is connected or respectively switched-on when there is a fall below a certain visible depth Z, and whereby the ventilating device is switched-off again when a certain visible depth A is exceeded. In addition, the output signal of the minimum of one photocell is fed to a comparator device, in which the output signal is compared with the electrical signals corresponding to both threshold values of the visible depths A or respectively Z. According in each case to the result of the comparison, an output signal is emitted, which, if necessary after suitable amplification, drives the ventilating device. Two-point controls of this type are known in themselves and are conventional, so that a detailed explanation of them is unnecessary. According to the invention, then, the visible depth between two predetermined threshold values is controlled, and the desired degree of purification is therefore adopted.

A fundamental advantage is that the (preferably used) photocells do not react to discolourations in the waste water, such as, for example, those produced by blood or testile dyes, but only to the intensity of the light coming through the waste water. In order to obtain reproducible results, this light originates preferably from an external light source.

According to FIG. 1, the switching point Z lies, for example, at a visible depth of 80 cm. and the switching point A at a visible depth 110 cm. In the case of smaller visible depths, i.e. when there is a fall below the threshold value Z of the visible depth, the ventilating device is switched on to nitrify the waste water-as indicated by the arrow N. When the threshold value A of a high visible depth is reached, the ventilating device is switched-off again, in order to achieve denitrification indicated by the arrow D. The visible depth, and therefore the oxygen content too, thus swings to and fro between the two threshold values A and Z. The switching points A and Z have thereby been experimentally determined in each case for a plant to be set in operation. As can be seen from the curve in FIG. 1, the slope of the curve changes in dependence on the degree of contamination. The switching frequency is thereby dependent on the desired degree of purification, i.e. on the respective visible depth values corresponding to the switching points and their distance apart. The arrows N and D thereby illustrate the performance setting.

It should be mentioned that when a waste water-activated sludge mixture is taken from an activating tank in operation for the purpose of determining visible depths, this removal can also be carried out intermittently, but will be suitably carried out continually.

Furthermore, particularly in the case of electrical control of the ventilating device, the switching signals are delayed accordingly to take into account the flow behaviour of the waste water to be purified.

Thus, there is disclosed a method of purifying an activated sludge waste water mixture which comprises the introduction of a gas comprising molecular oxygen to the mixture in automatically controlled manner in dependence upon the state of purification of the waste water. The state of purification is monitored simply (unlike known methods which require constant monitoring of the BOD of the mixture), by measuring the visible depth of the waste water. Depending upon this measurement, appropriate control is applied automatically over the (ventilation) introduction of the gas to the mixture.

A sample portion of an activated sludge-waste water mixture is taken from an activating tank in operation through a bypass arrangement, and the activated sludge present in the sample is separated in the bypass by an activated sludge separating device. The visible depth is then determined to control the ventilation intensity. Thereafter, the mixture is fed back to the activating tank, a ventilating tank or to a supply system of a sewage treatment plant.

Preferably, the visible depth is determined by a measuring device, and the ventilation intensity is adjusted thereafter. The arrangement may be such that control signals issued by the measuring device are delayed for a predetermined time period.

Figure 2:
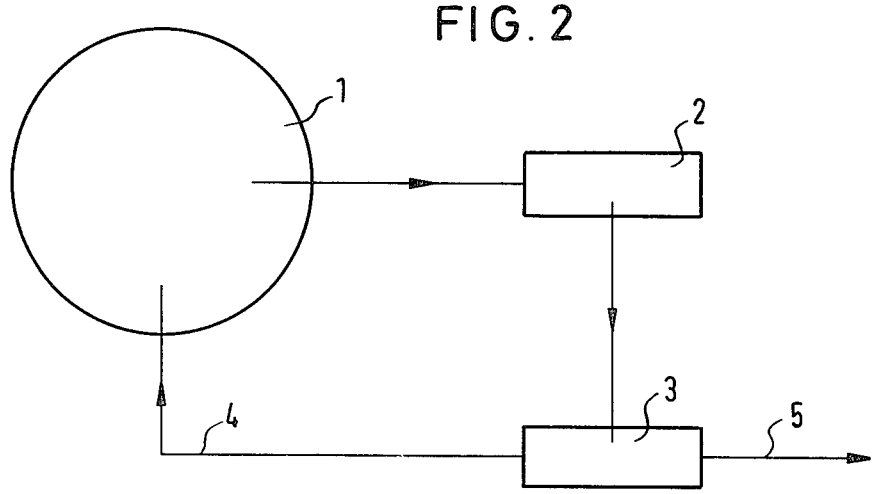
FIG. 2 is a schematic illustration of apparatus for carrying out the method according to the invention.

Referring now to FIG. 2 of the drawing, apparatus for purifying an activated sludge-waste water mixture comprises a tank for the mixture e.g. an activated sludge tank 1, a controllable ventilating device (5) for introducing automatically a gas comprising molecular oxygen to the mixture in dependence upon the state of purification of the waste water, a monitoring device (3) for measuring the visible depth of the waste water, and control means for controlling the operation of the ventilating device in dependence upon the measured value of the visible depth.

A sample portion of the mixture is removed from tank by an activated sludge separating device 2, and the monitoring device, shown schematically as a visible depth measuring device 3, measures the visible depth of the waste water. The measuring device 3 preferably comprises a photoelectric device having photo cells (to provide two point control known per se), and issues a control signal 5 in order to start, or stop, the operation of the ventilating device as appropriate (preferably after a predetermined time delay). A control water current is shown symbolically by reference 4.

It should be understood that FIG. 2 provides a schematic illustration only of the apparatus, which preferably has a bypass for extraction of a sample portion of the activated sludge waste water mixture, a removal device (2) in the bypass for effecting the extraction of the sample, a sludge separator (2) in the bypass to separate the activated sludge from the sample and comprising a centrifuge and/or a decanter, and a feed back device (2,3,4) for returning the removed mixture to the tank (1). The tank (1) may be an activating tank, a ventilating tank, a resettling tank or a part of a supply system of a sewage treatment plant.

I claim:

1. A method of purifying an activated sludge-waste water mixture, which comprises the introduction of a gas comprising molecular oxygen to the mixture in an automatically controlled manner in dependence upon the state of purification of the waste water;

in which the state of purification of the waste water is monitored by measuring the visible depth of the waste water and, depending upon this measurement, appropriate control is applied automatically over the introduction of the gas to the mixture.

2. A method according to claim 1, in which upper and lower visible depth threshold levels are set, and the introduction of the gas to the mixture is stopped and started respectively when the measured visible depth is below said lower threshold level and above said upper threshold level.

3. A method according to claim 1, in which a sample portion of an activated sludge-waste water mixture is removed from an activating tank, the activated sludge is separated from said sample portion of the mixture, and the visible depth of the remaining waste water is then measured in order to control the introduction of the gas to the remaining mixture in the activating tank.

4. A method according to claim 3, in which the activated sludge is removed from said sample portion in a by-pass arrangement by means of an activated sludge separating device.

5. A method according to claim 3, in which the activated sludge separated from the sample portion is returned to a ventilating tank or to a supply system of a sewage treatment plant.

6. A method according to claim 1, in which the visible depth is determined by a measuring device, and the intensity of ventilation of the mixture by the gas is adjusted thereafter.

7. A method according to claim 6, in which a predetermined time delay is provided between the determination of the visible depth and the control of operation of the introduction of the gas.

8. An activated sludge-waste water purifying apparatus comprising:

a tank for holding an activated sludge-waste water mixture;

a controllable ventilating device for introducing automatically a gas comprising molecular oxygen to said mixture in dependence upon the state of purification of the waste water;

a monitoring device for measuring the visible depth of the waste water;

and control means for controlling the operation of the ventilating device in dependence upon the measured value of the visible depth.

9. Apparatus according to claim 8, in which said monitoring device includes at least one measuring device.

10. Apparatus according to claim 9, in which said monitoring device includes a two-point control arrangement for switching-on or switching-off the ventilating device when predetermined values of the visible depth are reached.

11. Apparatus according to claim 8, including a device for removing a sample portion from the mixture in said tank, and a sludge separator for separating the activated sludge from said sample portion before the visible depth measurement is carried out.

12. Apparatus according to claim 11, including a feed-back device for returning the sample portion to said tank or to a supply system of a sewage treatment plant, after the visible depth measurement has been carried out.

13. Apparatus according to claim 11, in which the sludge separator comprises a centrifuge and/or a decanter.

* * * * *